United States Patent [19]

Antoniades et al.

[11] Patent Number: 5,035,887

[45] Date of Patent: Jul. 30, 1991

[54] WOUND HEALING COMPOSITION OF IL-1 AND PDGF OR IGF-1

[75] Inventors: Harry N. Antoniades, Newton; Samuel E. Lynch, Jamaica Plain, both of Mass.

[73] Assignees: Institute of Moelcular Biology, Inc., Boston; President and Fellows of Harvard College, Cambridge, both of Mass.

[21] Appl. No.: 403,969

[22] Filed: Sep. 7, 1989

[51] Int. Cl.$^5$ ............................................. A61K 37/36
[52] U.S. Cl. .................................... 424/85.2; 514/12; 514/21; 530/351
[58] Field of Search .................... 530/351; 514/12, 21; 424/85.2

[56] References Cited

U.S. PATENT DOCUMENTS

| | | | |
|---|---|---|---|
| 4,801,686 | 1/1989 | Kronheim | 530/351 |
| 4,849,407 | 7/1989 | Murray et al. | 514/12 |
| 4,861,757 | 8/1989 | Antoniades et al. | 514/21 |
| 4,874,746 | 10/1989 | Antoniades et al. | 514/21 |

FOREIGN PATENT DOCUMENTS

| | | | |
|---|---|---|---|
| 0312208 | 4/1989 | European Pat. Off. | |
| 032447 | 7/1989 | European Pat. Off. | 424/85.2 |

OTHER PUBLICATIONS

Martinet et al., J. Invest. Dermatol., 90: 122–126, 1988.
Bronson et al., Collagen Re. Res. 8: 199–208, 1988.
Grotendorst, J. Trauma 24: S49, (1984).
Leitzel et al., J. Dermatol. Surg. Oncol. 11: 617–22 (1985).
Michaeli et al., in *Soft and Hard Tissue Repair*, Hunt et al., eds., Praeger Publishers, N.Y., pp. 380–394, 1984.
Lynch et al., Proc. Natl. Acad. Sci. U.S.A. 84: 7696–7000, 1987.
Lynch et al., J. Clin. Invest. 84: 640–646, 1989.
Kaplan et al., Immunol. Res. 8: 118–129, 1989.

*Primary Examiner*—Howard E. Schain
*Attorney, Agent, or Firm*—Fish & Richardson

[57] ABSTRACT

Healing an external wound of a mammal by administering to the mammal a composition containing purified platelet-derived growth factor and purified interleukin-1 or administering to the mammal a composition containing purified insulin-like growth factor and interleukin-1.

10 Claims, No Drawings

WOUND HEALING COMPOSITION OF IL-1 AND PDGF OR IGF-1

BACKGROUND OF THE INVENTION

This invention relates to healing wounds.

Growth factors are polypeptide hormones which stimulate a defined population of target cells. Examples of growth factors include platelet-derived growth factor (PDGF), insulin-like growth factor (IGF-I), transforming growth factor beta (TGF-$\beta$), transforming growth factor alpha (TGF-$\alpha$), epidermal growth factor (EGF), and fibroblast growth factor (FGF), and interleukin-1 (IL-1). PDGF is a cationic, heat-stable protein found in the granules of circulating platelets which is known to stimulate in vitro protein synthesis and collagen production by fibroblasts. It is also known to act as an in vitro mitogen and chemotactic agent for fibroblasts, and smooth muscle cells.

It has been proposed to use PDGF to promote in vivo wound healing. For example, Grotendorst (1984) J. Trauma 24:549-52 describes adding PDGF to Hunt-Schilling wire mesh chambers impregnated with a collagen gel and implanted in the backs of rats; PDGF was found to increase the amount of new collagen synthesized. However, Leitzel et al. (1985) J. Dermatol. Surg. Oncol. 11:617-22 were unable to accelerate normal wound healing in hamsters using PDGF alone or in combination with FGF and EGF.

Michaeli, et al. (1984) In *Soft and Hard Tissue Repair* (Hunt, T. K. et al., Eds), Praeger Publishers, New York, pp. 380-394, report that application of a partially purified preparation of PDGF obtained from platelet-rich plasma stimulated angiogenesis when implanted in rabbit corneas. Because PDGF is not an angiogenic growth factor the investigators suggested that an unknown factor in their partially purified PDGF preparation was responsible for the angiogenic effect. Lynch et al, Role of Platelet-Derived Growth Factor in Wound Healing: Synergistic Effects with Other Growth Factors, Proc. Natl. Acad. Sci. U.S.A., Vol. 84, 7696-7700, and Growth Factors in Wound Healing (1989), J. Clin. Invest., Vol. 84, 640-646 demonstrated that purified PDGF preparations, including recombinant PDGF 2 preparations, did not produce a significant effect on connective tissue and epithelial layer regeneration in wound healing studies. In contrast, when purified PDGF was combined with either IGF-I, IGF-II or TGF-alpha a dramatic synergistic effect was seen both in connective tissue regeneration and re epithelialization. Application of IGF-I or II or TGF-alpha alone did not produce any significant effect in connective tissue and epithelial layer regeneration.

Interleukin-1 is a growth factor (or cytokine) which is produced naturally by several cell types, including lymphocytes and macrophages (Kaplan et al, Interleukin-1 and the Response to Injury, (1989) Immunol. Res., Vol. 8, 118-129. Purified, biologically active IL 1 has a molecular weight of about 17.5 Kd. It occurs in two forms (alpha and beta) with identical biological activity but significant differences in amino acid sequences. Here, the term "IL-1" includes both IL 1 alpha and IL 1 beta, as well as the larger precursor forms of both isoforms. IL-1 is characteristic for both neutrophils and mononuclear cells and stimulates fibroblast and keratinocyte proliferation in vitro, in tissue culture (Kaplan et al.). It is also chemoattractant for epidermal cells in vitro, in culture (Martinet et al., Identification and Characterization of Chemoattractants for Epidermal Cells, J. Invest. Dermatol., Vol. 90, 122-126, 1988) and induces changes in extracellular glycosaminoglycan composition (Bronson et al., Interleukin-1 Induced Changes in Glycosaminoglycan Composition of Cutaneous Scar-Derived Fibroblasts in Culture, Collagen Rel. Res., Vol 8, 1988, 199-208).

SUMMARY OF THE INVENTION

In general, the invention features healing an external wound in a mammal, e.g., a human patient, by applying to the wound an effective amount of a composition that includes a combination of purified PDGF and purified IL-1, or purified IGF-1 and purified IL-1. The IL 1 can be isolated from natural sources or, more preferably, produced by recombinant technology. The composition of the invention aids in healing the wound, at least in part, by promoting the growth of epithelial and connective tissue and the synthesis of total protein and collagen. Wound healing using the composition of the invention is more effective than that achieved in the absence of treatment (i.e., without applying exogenous agents) or by treatment with purified PDGF alone, purified IGF-1 alone, or purified IL-1 alone.

A preferred composition of the invention is prepared by combining, in a pharmaceutically acceptable carrier substance, e.g., commercially available inert gels, or membranes, or liquids, purified PDGF and IL-1 (both of which are commercially available). A second composition for promoting wound healing is prepared by combining purified IGF-1 and IL-1 in a pharmaceutically acceptable carrier. Most preferably purified PDGF and IL-1 or IGF-1 and IL-1 are combined in a weight-to-weight ratio of between 1:25 and 25:1, preferably between 1:10 and 10:1. The purified PDGF may be obtained from human platelets or by recombinant DNA technology. Thus, by the term "PDGF" we mean both platelet-derived and recombinant materials of mammalian, preferably primate, origin; most preferably, the primate is a human, but can also be a chimpanzee or other primate. Recombinant PDGF can be recombinant heterodimer, made by inserting into cultured prokaryotic or eukaryotic cells DNA sequences encoding both subunits, and then allowing the translated subunits to be processed by the cells to form heterodimer, or DNA encoding just one of the subunits (preferably the beta or "2" chain) can be inserted into cells, which then are cultured to produce homodimeric PDGF (PDGF-1 or PDGF-2 homodimer).

The term "purified" as used herein refers to PDGF IGF-1 or IL-1 which, prior to mixing with the other, is 90% or greater, by weight, PDGF, IGF-1 or IL-1, i.e., is substantially free of other proteins, lipids, and carbohydrates with which it is naturally associated.

A purified protein preparation will generally yield a single major band on a polyacrylamide gel for each PDGF, IGF-1 or IL-1 component. Most preferably, the purified PDGF, IGF 1 or IL-1 used in a composition of the invention is pure as judged by amino-terminal amino acid sequence analysis.

The compositions of the invention provide a fast, effective method for healing external wounds of mammals, e.g., bed sores, lacerations and burns. The compositions enhance connective tissue formation compared to natural healing (i.e. no exogenous agents added) or pure PDGF, IGF-1 or IL-1 alone. Unlike pure PDGF, IGF-1, or IL-1 alone, the composition of PDGF/IL-1 or IGF-1/IL-1 promotes a significant increase in both new connective tissue and epithelial tissue; the epithelial layer obtained is thicker than that created by natural healing or by IL-1 alone, and also contains more epithelial projections connecting it to the new connective tissue, making it more firmly bound and protective.

Other features and advantages of the invention will be apparent from the following description of the preferred embodiments thereof, and from the claims.

DESCRIPTION OF THE PREFERRED EMBODIMENTS

We now describe preferred embodiments of the invention.

External wounds, e.g., bed sores and burns, are treated, according to the invention, with PDGF/IL-1 or IGF-1/IL-1 mixtures prepared by combining pure PDGF and IL-1 or pure IGF-1 and IL-1. Natural or recombinant IL-1 is commercially available from R & D Systems, Minneapolis, Minnesota; Genzyme, Boston, Massachusetts; and Collaborative Research, Waltham, Massachusetts. Purified recombinant PDGF and purified PDGF derived from human platelets are commercially available from PDGF, Inc. (Boston, MA), Collaborative Research (Waltham, MA), Genzyme (Boston, MA) and Amgen Corp. (Thousand Oaks, CA). Purified PDGF can also be prepared as follows.

Five hundred to 1000 units of washed human platelet pellets are suspended in 1 M NaCl (2ml per platelet unit) and heated at 100° C. for 15 minutes. The supernatant is then separated by centrifugation and the precipitate extracted twice with the 1 M NaCl.

The extracts are combined and dialyzed against 0.08M NaCl–0.01M sodium phosphate buffer (pH 7.4) and mixed overnight at 4° C. with CM-Sephadex C-50 equilibrated with the buffer. The mixture is then poured into a column (5×100 cm), washed extensively with 0.08M NaCl–0.01M sodium phosphate buffer (pH 7.4), and eluted with 1M NaCl while 10 ml fractions are collected.

Active fractions are pooled and dialyzed against 0.3M NaCl–0.01M sodium phosphate buffer (pH 7.4), centrifuged, and passed at 4° C through a 2.5×25 cm column of Blue Sepharose (Pharmacia) equilibrated with 0.3M NaCl–0.01M sodium phosphate buffer (pH 7.4). The column is then washed with the buffer and partially purified PDGF eluted with a 1:1 solution of 1M NaCl and ethylene glycol.

The partially purified PDGF fractions are diluted (1:1) with 1M NaCl, dialyzed against 1M acetic acid, and lyophilized. The lyophilized samples are dissolved in 0.8M NaCl–0.01M sodium phosphate buffer (pH 7.4) and passed through a 1.2×40 cm column of CM-Sephadex C-50 equilibrated with the buffer. PDGF is then eluted with a NaCl radient (0.08 to 1M).

The active fractions are combined, dialyzed against 1M acetic acid, lyophilized, and dissolved in a small volume of 1M acetic acid 0.5 ml portions are applied to a 1.2×100 cm column of Biogel P-150 (100 to 200 mesh) equilibrated with 1M acetic acid. The PDGF is then eluted with 1M acetic acid while 2 ml fractions are collected.

Each active fraction containing 100 to 200 mg of protein is lyophilized, dissolved in 100 ml of 0.4% trifluoroacetic acid, and subjected to reverse phase high performance liquid chromatography on a phenyl Bondapak column (Waters). Elution with a linear acetonitrile gradient (0 to 60%) yields pure PDGF.

PDGF made by recombinant DNA technology can be prepared as follows.

Platelet-derived growth factor (PDGF) derived from human platelets contains two polypeptide sequences (PDGF-1 and PDGF-2 polypeptides; Antoniades, H. N. and Hunkapiller, M. (1983) Science 220:963–965). PDGF-1 is encoded by a gene localized in chromosome 7 (Betsholtz, C. et al , Nature 320:695–699), and PDGF-2 is encoded by the sis oncogene (Doolittle, R. et al. (1983) Science 221:275–277) localized in chromosome 22 (Dalla-Favera, L R. (1982) Science 218:686–688). The sis gene encodes the transforming protein of the Simian Sarcoma Virus (SSV) which is closely related to PDGF-2 polypeptide. The human cellular c-sis also encodes the PDGF 2 chain (Rao, C.D. et al. (1986) Proc Natl. Acad. Sci. USA 83:2392–2396). Because the two polypeptide chains of PDGF are coded by two different genes localized in separate chromosomes, the possibility exists that human PDGF consists of a disulfide-linked heterodimer of PDGF-1 and PDGF-2, or a mixture of the two homodimers (homodimer of PDGF-1 and homodimer of PDGF-2), or a mixture of the heterodimer and the two homodimers.

Mammalian cells in culture infected with the Simian Sarcoma Virus, which contains the gene encoding the PDGF-2 chain, were shown to synthesize the PDGF-2 polypeptide and to process it into a disulfide-linked homodimer (Robbins, K. et al. (1983) Nature 305:605–608). In addition, PDGF-2 homodimer reacts with antisera raised against human PDGF. Furthermore, the functional properties of the secreted PDGF-2 homodimer are similar to those of platelet-derived PDGF in that it stimulates DNA synthesis in cultured fibroblasts, it induces phosphorylation at the tyrosine residue of a 185 kd cell membrane protein, and it is capable of competing with human ($^{125}$I)-PDGF for binding to specific cell surface PDGF receptors (Owen, A. et al. (1984) Science 225:54–56). Similar properties were shown for the sis/PDGF-2 gene product derived from cultured normal human cells (for example, human arterial endothelial cells), or from human malignant cells expressing the sis/PDGF-2 gene (Antoniades, H. et al (1985) Cancer Cells 3:145–151).

The recombinant PDGF-2 homodimer (referred to as recombinant PDGF herein) is obtained by the introduction of cDNA clones of c-sis/PDGF-2 gene into mouse cells using an expression vector. The c-sis/PDGF 2 clone used for the expression was obtained from normal human cultured endothelial cells (Collins, T., et al. (1985) Nature 216:748–750).

Wound Healing

To determine the effectiveness of PDGF/IL-1 and IGF-1/IL 1 mixtures in promoting wound healing, the following experiments were performed.

Young white Yorkshire pigs (Parson's Farm, Hadley, MA) weighing between 10 and 15 kg were fasted for at least 6 hours prior to surgery and then anesthetized. Under aseptic conditions, the back and thoracic areas were clipped, shaved, and washed with mild soap and water. The area to be wounded was then disinfected with 70% alcohol.

Wounds measuring 1 cm×1.5 cm were induced at a depth of 0.7 mm using a modified Castroviejo electrokeratome (Storz, St. Louis, MO, as modified by Brownells, Inc.). The wounds resulted in complete removal of the epithelium, as well as a portion of the underlying dermis (comparable to a second degree burn injury). Individual wounds were separated by at least 15 mm of unwounded skin. Wounds receiving identical treatment were organized as a group and separated from other groups by at least 2 cm. Wounds receiving no growth factor treatment were separated from wounds receiving such treatment by at least 5 cm.

The wounds were treated directly with a single application of the following growth factors suspended in biocompatible gel: (1) 500 ng–1.0 μg pure recombinant PDGF-2 (purified by high performance liquid chromatography); (2) 500 ng-1.0 μg pure recombinant PDGF in combination with 500 ng-1.0 μg recombinant IL-1 alpha; (3) 500 ng-1.0 μg recombinant IL-1 alpha alone; (4) 500 ng-1.0 μg IL-1 alpha combined with 500 ng-1.0 μg of IGF-1; (5) 500 ng-1 μg IGF-1 alone.

Biopsy specimens were taken seven days after wounding.

Histologic Evaluation

Histologic specimens were prepared using standard paraffin impregnating and embedding techniques. Four micron sections were made and stained using filtered Harris hemotoxylin and alcoholic eosin; they were then observed under a microscope. All specimens were scored blindly by two investigators at equally distributed points throughout the sections. The widths of the epithelial and connective tissue layers were scored using a digitizing pad and drawing tube.

Results

The results from histologic evaluation indicated that wounds treated with the combination of purified recombinant PDGF and purified recombinant IL-1 had thicker connective tissue and epithelial layers, more extensive epithelial projections connecting these layers, and increased cellularity than wounds receiving no treatment, human IL 1 alone, or pure PDGF alone. Wounds treated with a combination of purified IGF-1 and purified IL-1 had thicker connective tissue layers and increased collagen fibers than wounds treated with IGF-1 alone or IL 1 alone. The total thickness of the newly synthesized wound tissue is shown in FIG. 1 and FIG. 2. The additive effects are indicated by the "open" portion of the bars and the effects above additive, i.e., synergistic effects, are indicated by the cross-hatched portion of the bars. The increase in the total thickness and cellularity of the newly synthesized tissue in wounds treated with either PDGF/IL-1 or IGF-1/IL-1 demonstrates that these treatments promote greater tissue growth and more rapid wound healing than would be predicted from the individual effects of these factors.

Other embodiments are within the following claims.

We claim:

1. A method for healing an external wound of a mammal comprising applying to said wound a wound healing amount of a composition comprising purified platelet-derived growth factor and purified interleukin-1.

2. A method for healing an external wound of a mammal comprising applying to said wound a wound healing amount of a composition comprising purified insulin-like growth factor I and purified interleukin-1.

3. The method of claims 1 and 2 wherein the weight to weight ratio of said platelet-derived growth factor or insulin-like growth factor to said interleukin-1 in said composition is between 1:25 and 25:1.

4. The method of claim 3 wherein said ratio is between 1:10 and 10:1.

5. A wound healing composition comprising purified platelet derived growth factor and purified interleukin-1, in a weight to weight ratio of 1:25 to 25:1.

6. The composition of claim 5 wherein said ratio is between 1:10 and 10:1.

7. A wound healing composition comprising purified insulin-like growth factor I and purified interleukin-1 in a weight to weight ratio of between 1:25 and 25:1.

8. The composition of claim 7 wherein said ratio is between 1:10 and 10:1.

9. A method for preparing a composition for healing wounds, comprising mixing purified platelet derived growth factor and purified interleukin-1 in a weight to weight ratio of between 1:25 and 25:1.

10. A method for preparing a composition for healing wounds comprising mixing purified insulin-like growth factor I or II and purified interleukin-1 in a weight-to-weight ratio of between 1:25 and 25:1.

* * * * *

UNITED STATES PATENT AND TRADEMARK OFFICE
CERTIFICATE OF CORRECTION

PATENT NO. : 5,035,887

DATED : July 30, 1991

INVENTOR(S) : Harry N. Antoniades and Samuel E. Lynch

It is certified that error appears in the above-identified patent and that said Letters Patent is hereby corrected as shown below:

On the Title page

Item [73] under "Assignees", correct the spelling of "Institute of Molecular Biology, Inc."

Signed and Sealed this

Fifteenth Day of December, 1992

Attest:

DOUGLAS B. COMER

*Attesting Officer*    Acting Commissioner of Patents and Trademarks